United States Patent [19]

Campbell

[11] Patent Number: 5,018,521

[45] Date of Patent: May 28, 1991

[54] METHOD OF AND APPARATUS FOR INCREASED TRANSFER OF HEAT INTO OR OUT OF THE BODY

[76] Inventor: William P. Campbell, 3310 Rowland Pl., Washington, D.C. 20008

[21] Appl. No.: 268,858

[22] Filed: Nov. 8, 1988

Related U.S. Application Data

[63] Continuation-in-part of Ser. No. 922,713, Oct. 24, 1986, abandoned.

[51] Int. Cl.⁵ .......................... A61F 7/00; A61N 1/00; A61H 1/00
[52] U.S. Cl. .................................. 128/363; 128/362; 128/399; 128/379; 128/384; 128/402
[58] Field of Search ............... 128/362, 363, 364, 365, 128/24.1, 379, 384, 385, 387, 386, 399, 400, 402, 403, 421, 422, 802, 803; 2/1, DIG. 1, DIG. 7; 272/73, 93

[56] References Cited

U.S. PATENT DOCUMENTS

| | | | |
|---|---|---|---|
| 1,305,439 | 6/1919 | Brennan | 128/402 |
| 3,075,517 | 1/1963 | Morehead | 128/24.1 |
| 3,296,819 | 1/1967 | Gough | 128/379 |
| 3,507,321 | 4/1970 | Palma | 128/400 |
| 3,610,250 | 10/1971 | Sarbacher | 128/379 |
| 4,523,594 | 6/1985 | Kuznetz | 128/399 |
| 4,580,983 | 4/1986 | Cassini et al. | 272/73 |
| 4,583,547 | 4/1986 | Granek et al. | 128/802 |
| 4,669,476 | 6/1987 | Gordon et al. | 128/399 |
| 4,676,246 | 6/1987 | Korenaga | 128/802 |
| 4,712,538 | 12/1987 | Hardie et al. | 128/24.1 |
| 4,718,429 | 1/1988 | Smidt | 128/400 |
| 4,747,408 | 3/1988 | Chuan-Chih | 128/400 |

FOREIGN PATENT DOCUMENTS

| | | | |
|---|---|---|---|
| 57-02148 | 7/1982 | Japan | 128/379 |
| 0725667 | 4/1980 | U.S.S.R. | 128/24.1 |

*Primary Examiner*—Edward M. Coven
*Assistant Examiner*—Jessica J. Harrison
*Attorney, Agent, or Firm*—Antonelli, Terry, Stout & Kraus

[57] ABSTRACT

Disclosed is a technique, and apparatus, for increasing flow of heat into or out of a person's body, wherein, simultaneously with the application of a heating or cooling medium to the body, the flow of blood to a surface region of the body is increased. The technique, and apparatus, can be used to increase burning (and rate of burning) of calories in the persons body, with resulting loss of fat and corresponding weight loss, by applying a cooling medium simultaneously with increasing flow of blood to a surface region of the body.

34 Claims, 11 Drawing Sheets

PIN 2 
PIN 3

METHOD OF AND APPARATUS FOR INCREASED TRANSFER OF HEAT INTO OR OUT OF THE BODY

This application is a continuation-in-part application of application Ser. No. 922,713, filed Oct. 24, 1986, now abandoned.

BACKGROUND OF THE INVENTION

The present invention relates generally to a method and apparatus for increasing heat transfer to and from a body (more specifically, to and from the body of a person). Such increased heat transfer has a use for increasing the burning of calories by a person, and other treatments of a person where transferring heat to (or removing heat from) the body is appropriate.

More particularly, the present invention is directed to a method of, and apparatus for, increased burning of calories, which can cause loss of fat and resulting weight loss in a person. Thus, the present invention can be utilized for losing weight.

In addition, the present invention can also be utilized for treating a body so as to speedily transfer heat to (or remove heat from) a body, for example, for treating hypothermia or hyperthermia.

It has been proposed to increase the burning of calories in a body, so as to help a person lose fat independent of any exercise. See Pearson, et al., *The Life Extension Weight Loss Program* (pub. by Doubleday & Co. 1986), particularly pages 144-164 thereof ("Thermogenesis: The Cool Way to Lose Fat"), which pages 144-164 are incorporated herein by reference in their entirety, and which pages 144-164 disclose that increased burning of calories in a body, e.g., by transferring heat out of the body (e.g., cold-induced thermogenesis) causes loss of fat, which can result in weight loss. The pages of this publication incorporated herein generally disclose the technique of thermogenesis (i.e., generation of heat) and describe how such technique can be used for causing loss of fat in a person's body.

U.S. application Ser. No. 922,713, filed Oct. 24, 1986, the contents of which are incorporated herein by reference in their entirety, discloses that cold-induced thermogenesis can be utilized to increase burning of calories, with a resultant loss of fat and corresponding weight loss, and that such cold-induced thermogenesis can be achieved not only by cooling the environment so as to cool a person's body totally, but also by cooling part of the anatomy of a person. In particular, application Ser. No. 922,713 discloses that by applying a cooling medium to part of the human anatomy, thermogenesis can be induced, so as to increase the burning of calories, and to cause loss of fat and thereby cause weight loss. This patent application discloses that such fat is lost generally from the body, and not only at the location at which the cooling medium is applied.

This patent application Ser. No. 922,713 discloses that various known devices can be utilized for application of a cooling medium to part of an anatomy; and that known, commercial devices can be used in a new way so as to increase burning of calories, with a resulting weight loss.

U.S. patent application Ser. No. 922,713 further discloses that the commercial devices, utilized for increasing the burning of calories, can be used in conjunction with other weight loss techniques, such as exercising, to induce even further weight loss and provide other benefits, such as cardiovascular conditioning.

As for various known devices for application of a cooling medium to part of a person's anatomy, U.S. Pat. No. 4,326,533 to Henderson discloses body cooling devices having at least one pocket for receiving and storing a container of frozen liquid or semi-liquid material. The disclosed cooling device is in the form of an elasticized or manually adjustable band of soft textile material, which has at least one compartment with at least one opening into which individual bags or containers of frozen liquid or semi-liquid material are placed for use and subsequently removed, when melted, for refreezing and reuse, the device being particularly suited to be worn around the head or wrists to thereby reduce body heat and absorb perspiration of those engaged in physical effort (such as sport participants and workers). This patent discloses that this device is also suited for cooling various parts of the body for medical purposes.

U.S. Pat. No. 2,288,745 to Sammis discloses a device and method for assisting a person to keep comfortable in warm or hot weather, assisting the body to dissipate excess heat. The disclosed device includes a fabric bag or envelope to which is suitably fastened an elastic arm band, with a sponge rubber container or sack removably mounted in the bag, the sack being slit along a portion of its periphery which opens into a chamber or compartment inside of the sack, and with a cake or cube of a suitable refrigerant, such as dry ice, being provided in the chamber or compartment.

U.S. Pat. No. 2,208,855 to Riley discloses a temperature reducing material, wherein a suitable refrigerant is dispersed throughout a suitable inert porous carrier prior to utilization for temperature reducing purposes, the intimate combination of refrigerant and carrier providing the temperature reducing material. In a specific embodiment, this patent discloses using a combination of a frozen substance, such as ice, with a natural or cellulosic sponge material, the substance being frozen from a controlled quantity of the same dispersed throughout the porous body of the sponge.

While each of the foregoing patents disclose various apparatus for application of a cooling medium to part of the anatomy, none of these patents disclose that the application of the cooling medium can be utilized to induce thermogenesis, and, in particular, none of these patents disclose application of the cooling medium to increase burning of calories so as to cause loss of fat. Furthermore, none of these patents disclose increased burning of calories, for purposes of losing weight, through use of the disclosed devices.

Moreover, in using the devices disclosed in these three patents, particularly for purposes of increasing the burning of calories, the following problem arises. When applying the disclosed devices, whereby the temperature at that specific portion of the body is lowered, the body tries to limit heat loss by constricting the flow of blood to the outer layers of the body at such point. Accordingly, the amount of heat transferred from the body, and the rate of transfer of the heat, is reduced. Thus, while placing the body in a cooler environment will result in increased calorie consumption to some extent, the amount of increased calorie consumption is reduced, and the amount of time necessary for such increased calorie consumption unduly increases, due to the constricting of the flow of blood to the cooled locations. To practically lose a large amount of fat via this method a person must remain in what may be an uncomfortable setting for an extended period of time.

Moreover, it has been shown that a main difference between overweight persons, and persons of normal weight, is that the overweight person is less efficient at losing heat to the environment. Also, it has been shown that shutting down the capillaries in the outer areas of the body on a regular basis (which would occur upon utilizing a localized, or even general, cooling of the body on a regular basis) can lead to long-term thermogenesis inefficiency. Thus, for using thermogenesis as a technique for causing fat loss (e.g., in a dieting program), it is desired to increase the transfer of heat from the body, and to more efficiently transfer such heat (for example, at a higher rate of transfer).

Generally, in treatment of persons wherein transfer of heat to and from a person's body is used (for example, in treatment of persons suffering from hypothermia or hyperthermia), it also becomes important to transfer heat to (or remove heat from) a person's body more efficiently, in greater amounts and at a faster rate.

In Clinical Electrotherapy (ed. by Nelson & Currier and pub. by Appleton & Lang 1987), pages 156–8, it is disclosed that long- and short-term electrical stimulation of muscle results in an increased vascular supply, with a concomitant increase in the number of capillaries within the muscle. Thus, this article discloses that over 4-, 14- and 28-day periods of intermittent electrical stimulation (10-Hz frequency), it has been reported that there is a 20-, 50- and 100-percent increase in capillary density to the stimulated tissue, respectively. This article discloses the effect of electrical stimulation on blood flow, and not uses of such effect.

Accordingly, it is still desired to improve transfer of heat to or from a body (that is, transfer heat or cold from a source of such heat or cold to the body), for purposes of treatment of the body (e.g., to alleviate hyperthermia or hypothermia), or to increase transfer of heat from the body so as to increase burning of calories for causing increased loss of fat and weight loss.

SUMMARY OF THE INVENTION

Accordingly, it is an object of the present invention to provide increased transfer of heat to or from a body, from a source of cold (or of heat), and to provide an increased rate of such transfer.

It is a further object of the present invention to provide apparatus which can be utilized to increase the transfer of heat to or from a body, from a source of cold (or of heat).

It is a further object of the present invention to increase the burning of calories by a body, by increasing the transfer of heat from the body (that is, increasing the transfer of heat out of the body).

It is a further object of the present invention to provide a method, and apparatus, for providing loss of fat and resulting weight loss, by increased burning of calories due to increased transfer of heat from the body.

It is a further object of the present invention to treat a person (e.g., to avoid or treat hyperthermia or hypothermia), by increasing the transfer of heat to or from the body, from a source of cold (or of heat).

The present invention achieves each of the above objects by utilizing, in combination with application of heat (or of cold), a means for increasing the supply of blood to a surface region of the body, so as to increase the flow of blood to locations near the skin surface, whereby transfer of heat to or from the body can be increased, and the rate of transfer of such heat to or from the body can be increased.

By the present invention, not only can localized heat or cold be applied, but the body can be subjected generally to a source of heat or cold (e.g., immersed in a medium which is at a temperature above or below that of the body's core temperature), to effect the heating or cooling.

Thus, generally, the present invention involves application of heat or cold, either localized or generally, to a person's body, together with application of a means for increasing the flow of blood to a surface region of the body, to increase transfer of heat to or from the body.

Generally, the present invention is not limited to a specific technique for increasing the flow of blood toward the skin surface (to a body surface region). Preferably, the technique can be an electro-stimulation technique or a chemical technique. Furthermore, minor irritation of the skin can be used for increasing blood flow to body surface regions. Moreover, the means for increasing blood flow toward a surface region of a person's body can be applied at various locations over a person's body.

When electro-stimulation is utilized for increasing blood flow toward the surface, the electrode means can be held in electrical contact with desired muscle groups, so as to increase blood circulation thereto and provide increased flow of blood to the surface region, for transfer of heat or cold.

Furthermore, chemical means for maintaining a relatively low, or relatively high, pH in contact with the skin can be utilized for increasing flow of blood toward the skin, for increased heat or cold transfer. Illustratively, the chemical means should be non-irritating to the skin, and can be either below neutral (pH of below 7) or above neutral (pH of above 7) so as to increase flow of blood toward the surface regions of the body. As the pH of the material is lowered further below 7, or raised higher above 7, irritation of the skin should be avoided. The chemical means can be a liquid-soaked pad (e.g., a saturated sponge), the liquid having desired pH levels.

Moreover, multiple techniques can be used in concert for increasing blood circulation to surface regions of the body. For example, an electrically conducting, saturated sponge (saturated with a liquid having a pH less than 7, providing electrical conductivity to the saturated sponge) can be used both as an electrode for electro-stimulation purposes and as a relatively low pH pad, for increasing blood flow toward surface regions of the body.

The means for increasing blood flow in a surface region of a body, for purposes of increasing heat or cold transfer, can be incorporated as part of various types of wearing apparel. For example, the means for increasing blood circulation toward the skin surface can be incorporated in a belt, vest or mesh suit. Moreover, it is preferred that such belt, vest or mesh suit be made at least in part of elastic material, so as to hold the electrodes (of the electro-stimulation apparatus), or to hold the means for maintaining the pH at a relatively low (or relatively high) level adjacent the skin, tightly in contact with the skin.

Accordingly, by the present invention, increased flow of blood toward the skin surface, together with application of heat or cold to the body, can be used in combination to provide various advantageous benefits.

For example, an enhanced thermogenesis can be achieved.

Specifically, application of heat or cold (either locally or generally), together with application of means for increasing flow of blood toward the skin surface, can be utilized to treat or prevent hypothermia or hyperthermia, respectively.

Moreover, application of cold, together with application of the means for increasing flow of blood toward the skin surface, can be utilized to increase burning of calories, to thereby increase loss of fat and cause resultant loss of weight. Thus, an enhanced thermogenesis is achieved. The present technique can be utilized by itself (without exercising, e.g., simultaneously exercising) in a weight loss program, or can be utilized concurrently with exercising to improve the cardiovascular system and cause weight loss.

DETAILED DESCRIPTION OF THE INVENTION

While the present invention will be described in connection with specific and preferred embodiments, it will be understood that it is not intended to limit the invention to those embodiments. On the contrary, it is intended to cover all alterations, modifications and equivalents as may be included within the spirit and scope of the invention as defined by the appended claims.

Generally, the present invention contemplates application of heat or cold to the body, in combination with increasing flow of blood to surface regions of the body, to increase transfer of heat to or from the body. The present invention also contemplates that certain advantageous effects can be achieved through use of such increased transfer of heat to or from the body. Thus, the technique of increasing blood flow near the skin surface, while applying a cooling medium to the body, can be utilized for increasing burning of calories by the body with resultant loss of fat and weight loss. Moreover, such application of heat or cold, together with increasing the flow of blood to locations close to the skin surface, can be used to treat or prevent hypothermia or hyperthermia.

As a most preferred technique for increasing blood flow to surface regions of the body, electro-stimulation (for example, electrical stimulation of muscle groups) can be utilized. Such electrical stimulation, as discussed in the aforementioned article in *Clinical Electrotherapy* (the contents of which have been incorporated herein by reference), in a 1-10 Hz range can be utilized to provide the most preferred increased blood flow.

Figure 1:
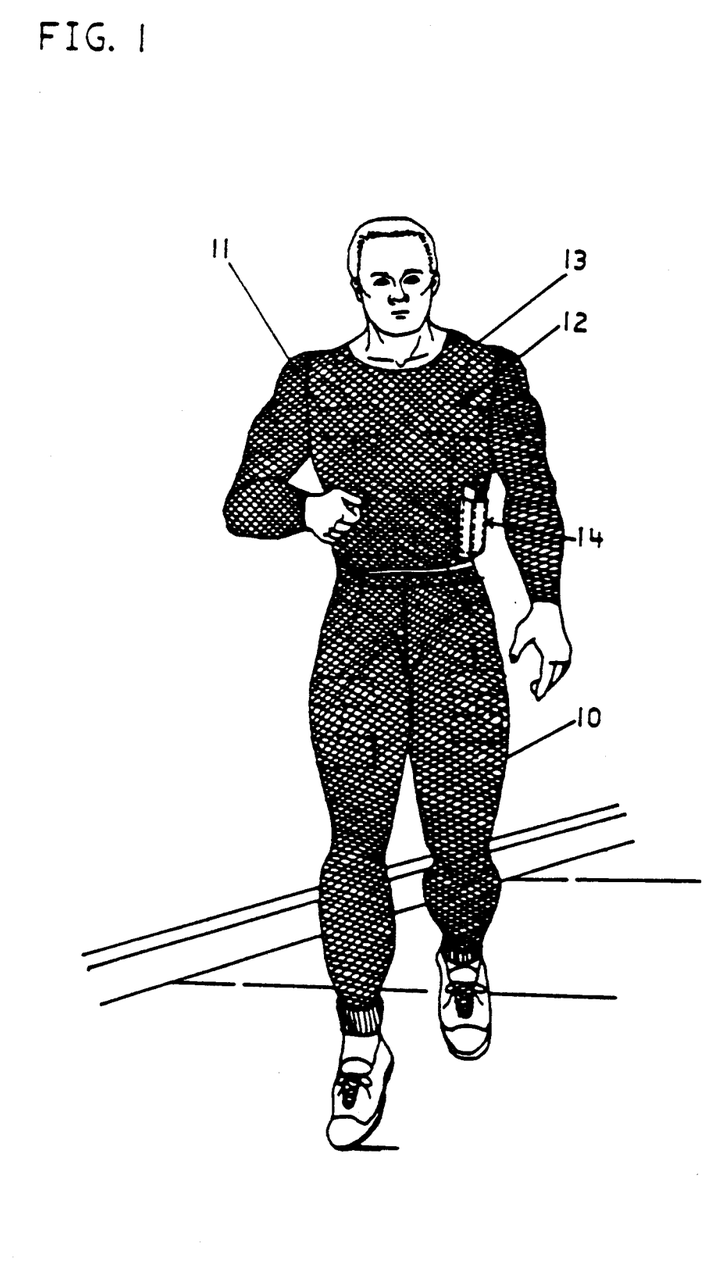
FIG. 1 shows a first embodiment of the present invention, wherein the means for increasing flow of blood toward the skin surface is incorporated in a full mesh suit covering a person's body.

FIG. 1 illustrates a first embodiment of the present invention, wherein the electrical stimulation means is incorporated in a full body suit. In this FIG. 1, air or water (surrounding the person) can be used as a medium for removing heat from or transferring heat to the person's body, with the mesh suit 10 providing a substrate for mounting the electrode means of the electrical stimulation means. Preferably, the mesh suit 10 is made of an elastic material so as to hold the electrodes 11 tightly in contact with the skin.

In FIG. 1, the electrode means 11 can be positioned to conform with a specific position on the suit, and hence be held in electrical contact with desired muscle groups by means well known in the art, such as, for example, a safety pin 12 electrically connected to wire means 13 which could pass through the mesh suit and through the electrode means thereby holding the wire means and electrode means in the desired position while providing electrical continuity with the electrode means. The wire means interconnects half of the electrodes to one electric pole of an electric pulse generator means 14, which electric pulse generator means, including circuitry therefor, is known in the art. The other half of the electrodes are likewise interconnected with the opposite pole of the pulse generator 14. By this apparatus, pulsed current passes from one half of the electrodes (one of the two groups of electrodes) through the body to the other half of the electrodes (the other group of electrodes), to stimulate increased blood flow to body surface regions.

Figure 11:
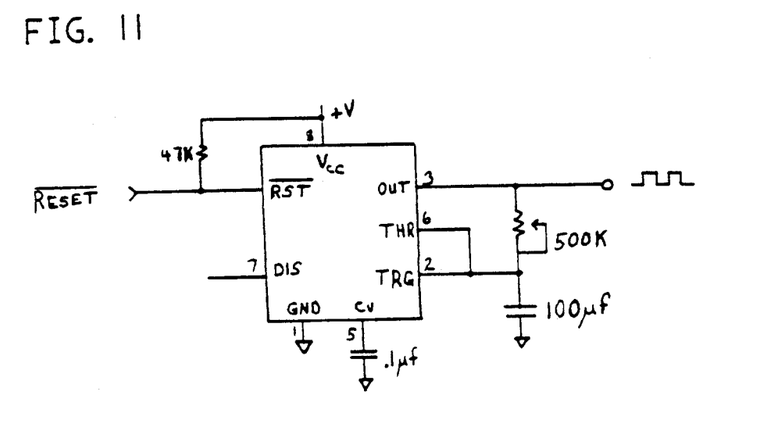
FIGS. 11-13 show circuitry and current output waveform, illustrative for increasing blood flow to body surface regions by electrical stimulation.
Figure 12:
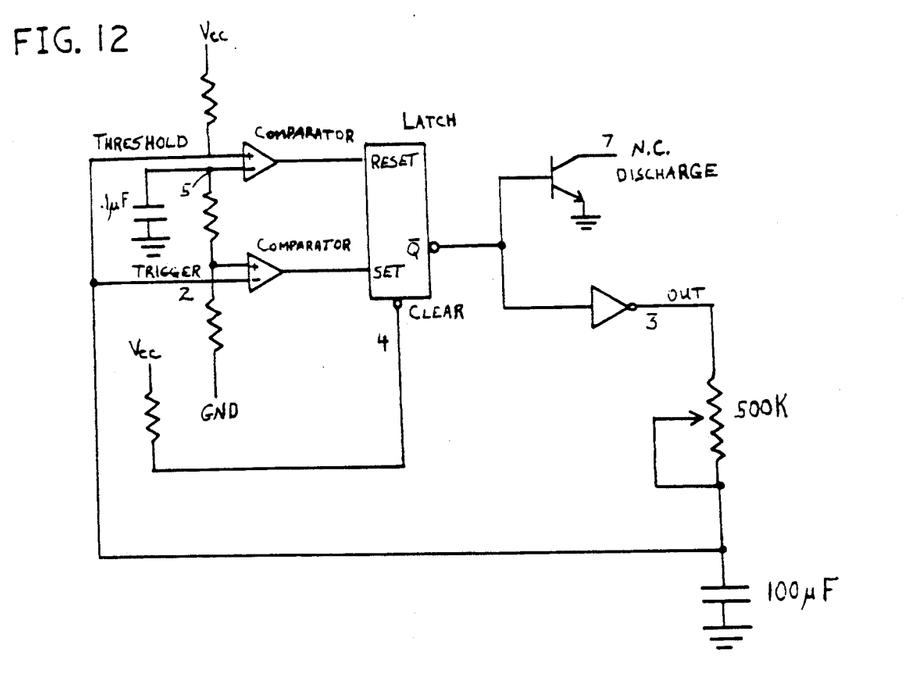
Figure 13:
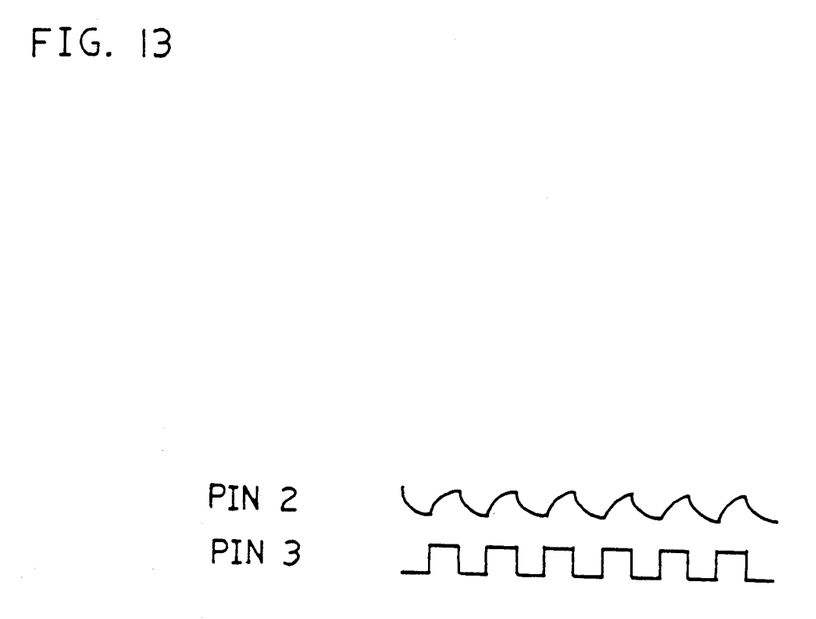

A pulse circuit which can be used in connection with the electrical stimulation of the present invention is illustrated in FIGS. 11-13. Shown in FIG. 11 is a generic integrated circuit timer chip (illustrative of IC timer chips made by National Semiconductor, Texas Instruments, Fairchild, etc.) based on two, voltage comparators and a set/reset latch (sometimes called a flip-flop) The inputs, "threshold" and "trigger", of the comparators typically monitor the voltage on a timing capacitor. An internal voltage divider made of three resistors connected in series from $V_{cc}$ (the most positive voltage potential) to ground provides fixed references of $\frac{2}{3} V_{cc}$ and $\frac{1}{3} V_{cc}$ to the comparators. The outputs of the comparators are connected to the set and re-set inputs of the flip-flop The flip-flop controls the polarity of an inverting "push/pull" output stage (whose output is labelled "out") and an open collector transistor switch connected to the pin labelled "discharge". Generally, the transistor (shown in FIG. 12) is connected to the timing capacitor. However, if the pulse width need not be as precisely controlled, the capacitor could be electrically connected to the pin marked "out", as shown in FIG. 11.

The pin labelled "reset" (see FIG. 12) is connected to the latch inhibit/reset input and is used to end a pulse, force the "out" pin low, discharge the timing capacitor, etc. The pin labelled "control voltage" (C.V. in FIG. 11) is used to force the voltage references of the comparator to be C.V. and $\frac{1}{2}$ C.V. "Reset" is not used in FIG. 11.

A description of the operation of the pulse circuit will be provided with reference to FIG. 12. At start up, the voltage on the capacitor is zero. When $V_{cc}$ reaches a level that allows the integrated circuit to operate, the output of the comparator connected to "trigger" goes high and sets the latch, the "Q bar" (inverted output) signal goes low, the push/pull inverter output goes high, and the 100 μF capacitor begins to charge through the 500K ohm potentiometer. The rate of charge and hence the frequency of the waveforms is dependent on the resistance of the potentiometer. When the voltage at the "trigger" input passes the reference of $\frac{1}{3} V_{cc}$, the latch input goes low. The output does not change until the capacitor charge to slightly more than $\frac{2}{3} V_{cc}$. At this time, the output of the comparator connected to the "threshold" input goes low, the flip-flop is reset, and the capacitor begins to discharge. This cycle repeats and the waveforms in FIG. 13 are generated. The 0.1 µF capacitor connected to pin 5 filters out noise and unwanted alternating current from the voltage references. The 47K ohm pull-up resistor connected to the reset input is used to turn off this feature of the integrated circuit.

Known power sources, having various different waveforms, can be used in accordance with this aspect of the present invention. For example, a pulse generator having its own power pack can be used. Illustrative waveforms of the power source output include (but are not limited to) alternating current, direct current, biphasic, square wave, sine wave, triangular wave, etc.

In operation of the device of the present invention, the user, after donning the suit and positioning the electrode means, situates him or herself in a fluid medium such as, for example, air or water. For the purpose of enhanced thermogenesis, this medium should be at a temperature below or above that of the core temperature of the body (which core temperature is normally 98.6° F). The electric pulse generator means is then turned on. Illustratively, the generator means 14 applies pulses at a rate of between 1 pulse/ten minutes and 100,000 Hz, preferably between 1-10 Hz. These pulses have a pulse width of between 0.01-60,000 microseconds, and preferably between 30-300 microseconds, and an amplitude of between 0.001-2,000 milliamperes, with a preferred range of between 0.5-140 milliamperes. The electric pulses pass via the wire means 13 and electrode means 11, thereby causing the capillaries to open and increasing blood flow to surface regions of the body, and overriding the normal constricting effect of application of cold temperatures. The application of the electric pulses also causes rhythmic contractions of the muscles which in turn cause a further increase in blood flow. These combined actions serve to greatly increase the ability of the body to exchange heat with the environment. When the core temperature of the body drops below the normal 98.6° F. temperature, the body starts conversion of stored fat into heat, thereby producing loss of fat with a resulting weight loss.

Figure 2:
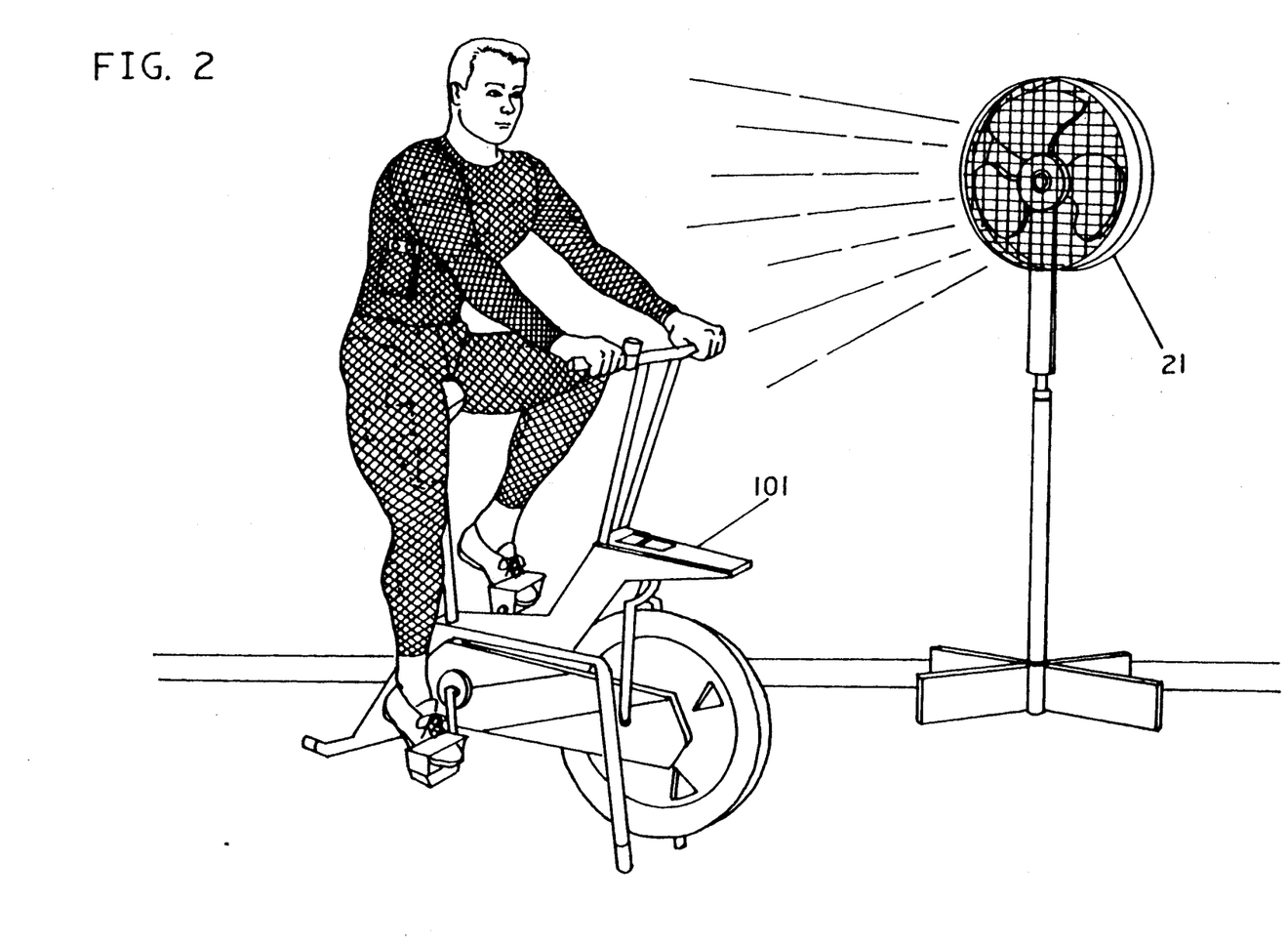
FIGS. 2 and 3 show use of the present invention during exercise.
Figure 3:
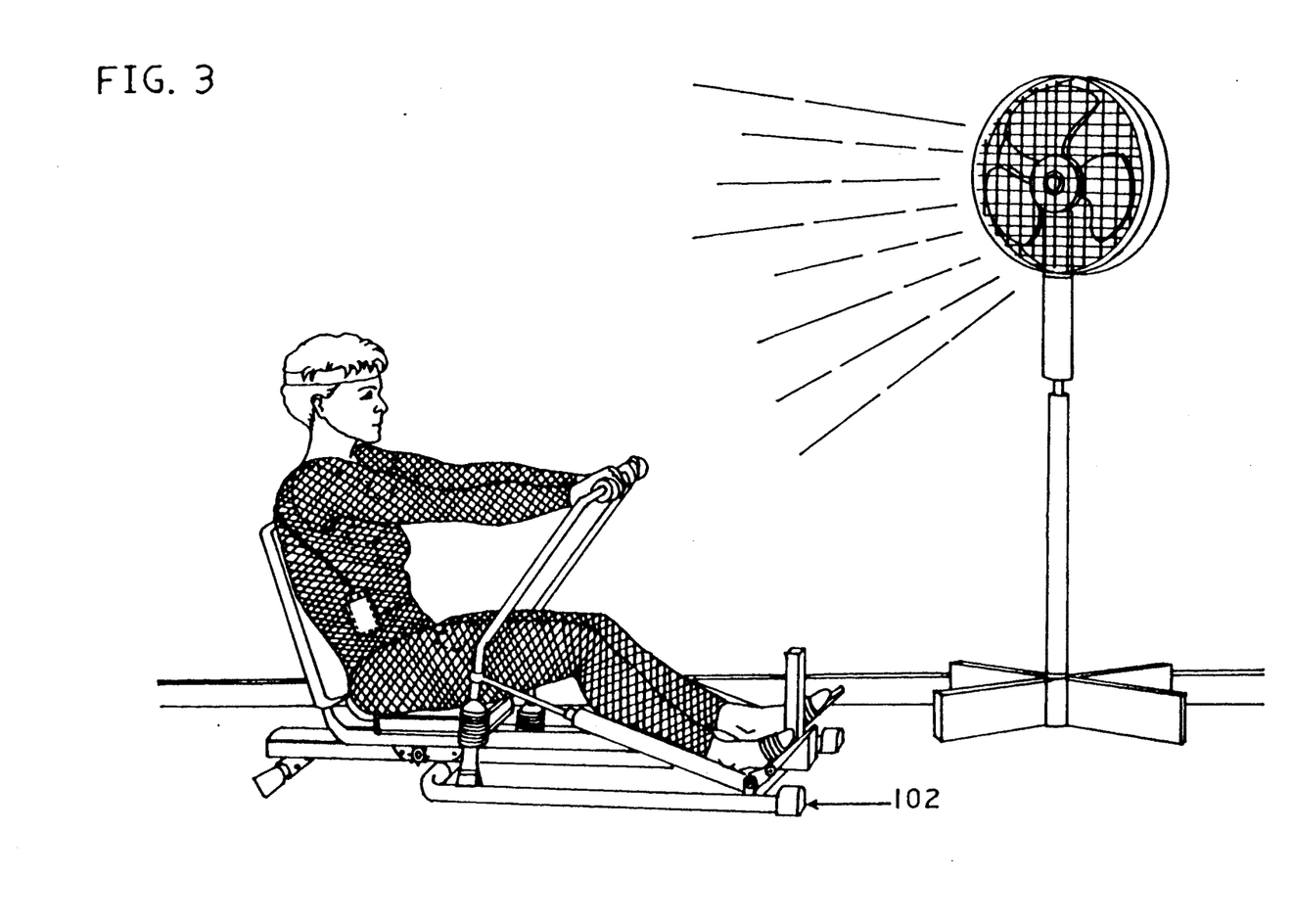

As seen in the foregoing, a mesh body suit 10 is utilized in FIG. 1. Such mesh design is preferred, since it permits the body to be exposed to the, e.g., cooling medium in which it is located. However, such substrate for the electrodes need not be a mesh suit, as long as transfer of, e.g., cold from the environment can be achieved. Of course, it is preferred that transfer of cold not be impeded, to any substantial extent, by the substrate for mounting the electrodes FIG. 2 and FIG. 3 illustrate the use of a fan or propeller 21 to force circulation of the fluid medium over the body of the user; similarly, FIG. 1 shows the user of the device jogging. By use of such fan or propeller, during operation of the device, or by moving (for example, by jogging) during operation of the device, air circulation around the person's body increases, further increasing the transfer of heat from the body (or transfer of heat to the body, where the fluid medium is warmer than the body core temperature) while using the device.

Of course, while circulation of air is described in connection with each of FIGS. 1-3 (with FIGS. 2 and 3 showing forced circulation of air), such circulation of air is not required, although it does increase the exchange of heat with the environment.

Each of FIGS. 2 and 3 show operation of the device during use of exercise equipment. Specifically, FIG. 2 shows use of the device while exercising on a stationary bicycle 101, while FIG. 3 shows use of the device while exercising on rowing machine 102. In view of ease of use of the present device to increase blood flow to surface regions of the body, the device can be worn during other types of exercise, also. For example, if the pulse generator is enclosed is a water-proof enclosure, the device could also be used when a person is swimming. Thus, for example, a mesh body suit 10 as in FIG. 1 can be used as a substrate during swimming, with the water (at a temperature below 98.6° F.) being used as the fluid medium for transfer of heat from the body, to provide enhanced thermogenesis and thus increase burning of calories and loss of fat, with resultant weight loss.

Figure 4:
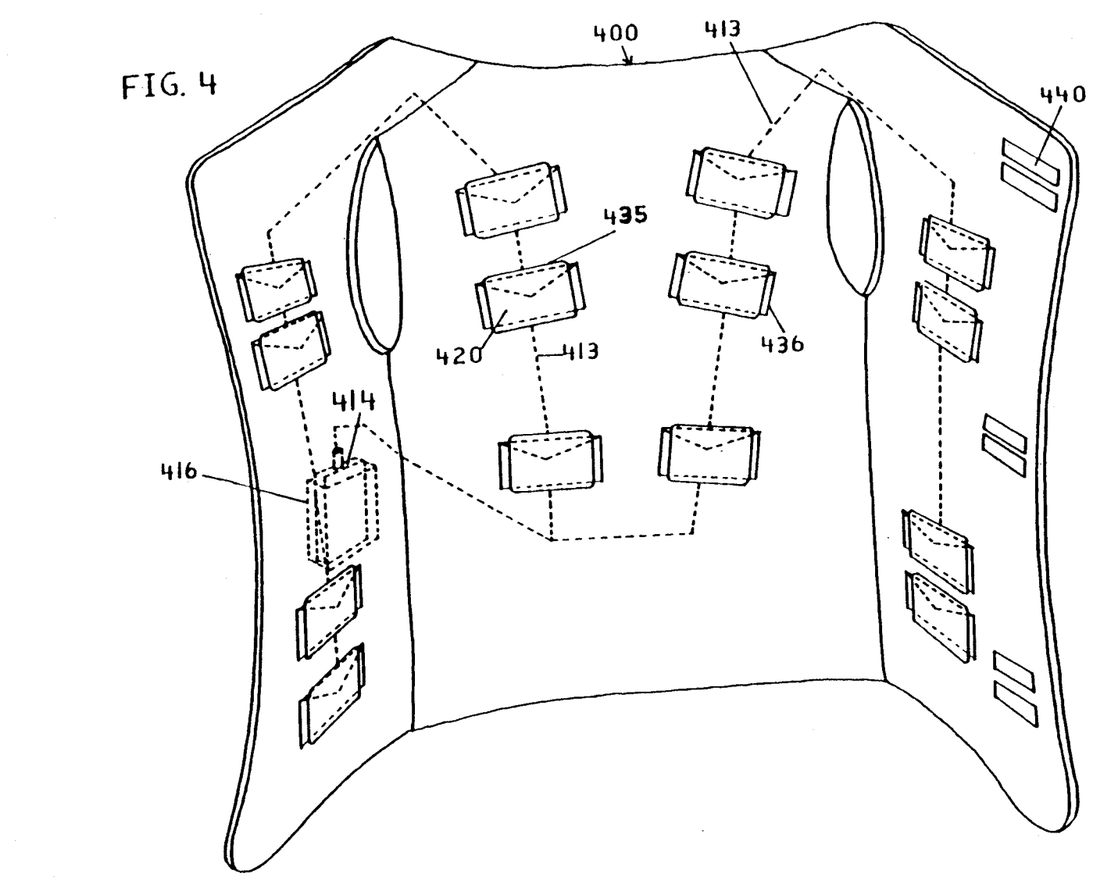
FIGS. 4-6 show a second embodiment of the present invention, wherein the means for increasing blood flow toward the skin surface is incorporated in a vest.
Figure 5:
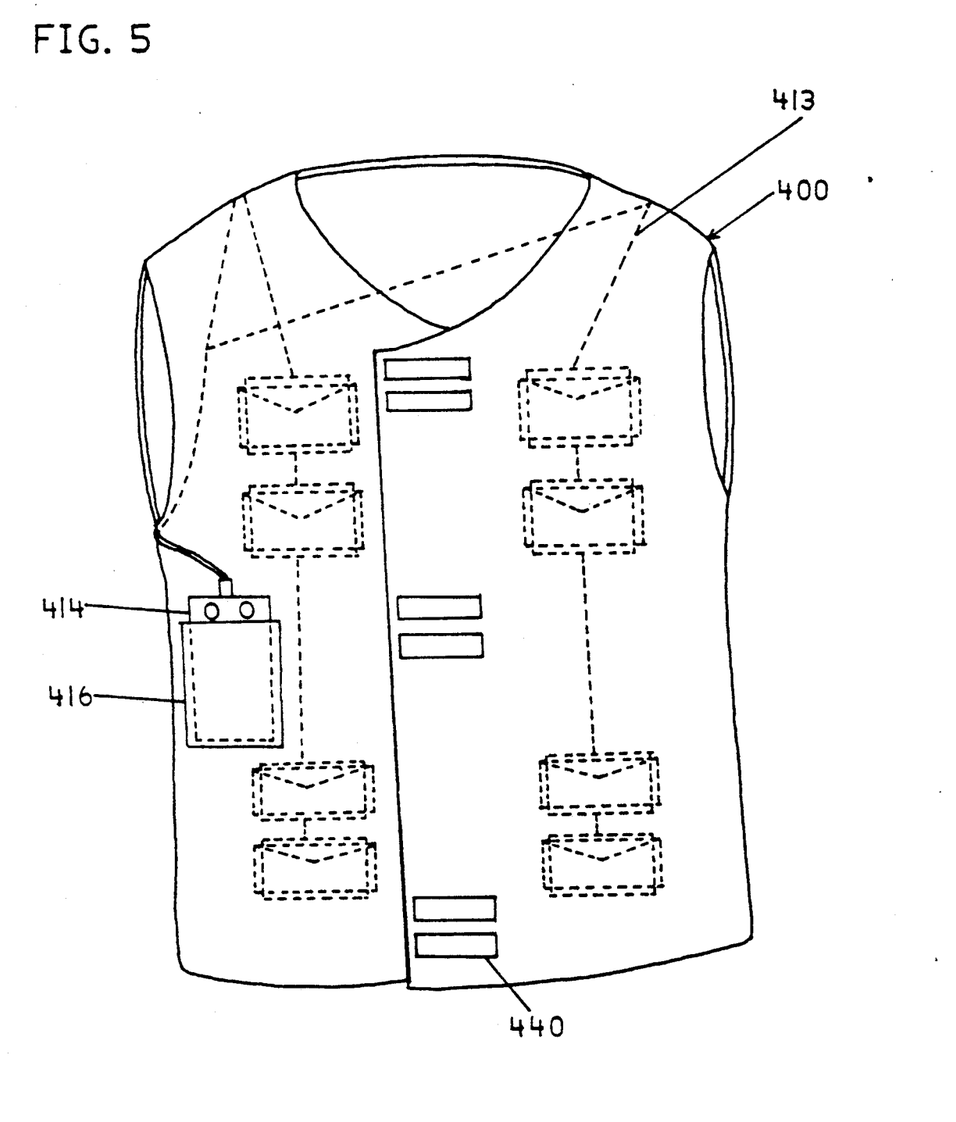
Figure 6:
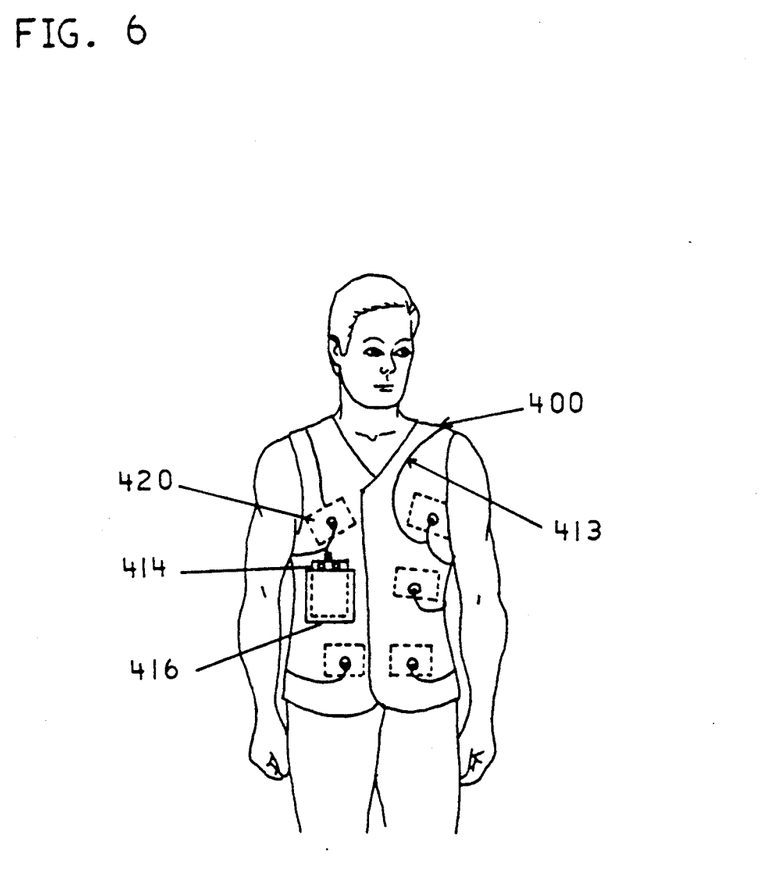

FIGS. 4-6 show another embodiment of the present invention, wherein an electric stimulator device, for increasing flow of blood to surface regions of the body, and cold or warm material for localized application to the body for removing heat from the body thereby to increase burning of calories, or to add heat to the body, are contained in a vest. FIG. 4 shows vest 400 with holding means 416 (for example a pocket) for holding a pulse generator 414 (note, especially, FIGS. 5 and 6). Wire means 413 extend from the pulse generator to electrode means 420, each of which electrode means 420 is mechanically attached to the vest. At the location of the electrodes, as shown in FIG. 4, is a retention means 435 for holding a packet of cold material 436, preferably a material which remains flexible when frozen. Thus, by this aspect of the present invention, both the cold material and electrical stimulation are applied locally, and are applied generally to the same area of the body. Of course, a heated material can be substituted for cold material 435, to locally apply heat.

The cold material 435 can be replaceably located in retention means 436. For example, cold material can be cooled (e.g., in a refrigerator) and then placed in retention means 436. After the cold material has warmed up during operation of the device, it can be removed and returned to the refrigerator for further cooling. Such replaceable cold material is described in the aforementioned U.S. patent application Ser. No. 922,713, filed Oct. 24, 1986. A replaceable hot material can also be used.

The vest also includes fastening means 440, such as of Velcro, for fastening the vest while on the body. Furthermore, it is preferred that the vest be made of an elastic material, so that it can have an even tighter fit and therefore hold the electrodes against the body. FIG. 5 shows this vest from the outside, while closed, and FIG. 6 shows the vest worn by a person. In FIGS. 5 and 6, elements denoted by the same reference characters are the same as described in connection with FIG. 4.

Figure 7:
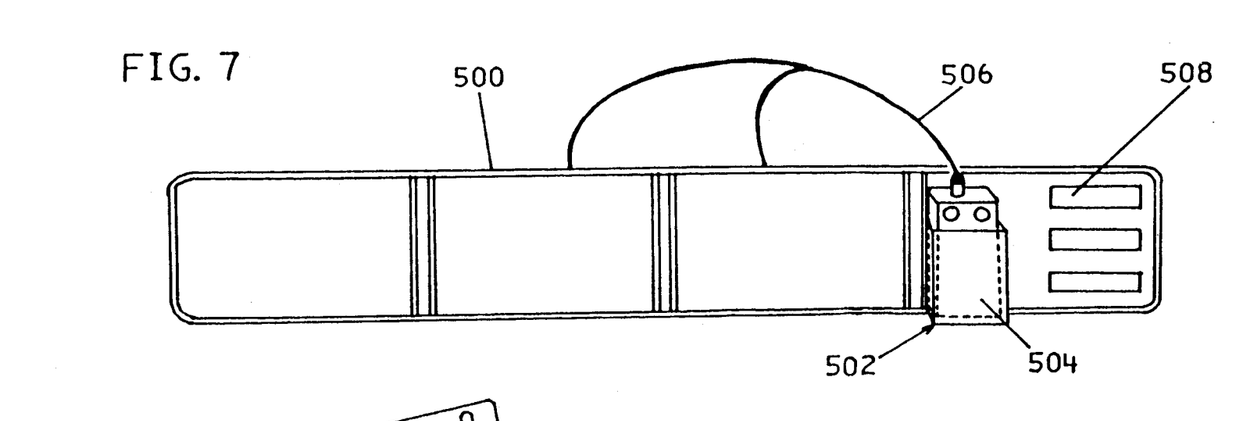
FIGS. 7-10 show a third embodiment of the present invention, wherein the means for increasing flow of blood toward the skin surface is incorporated in a belt.
Figure 8:
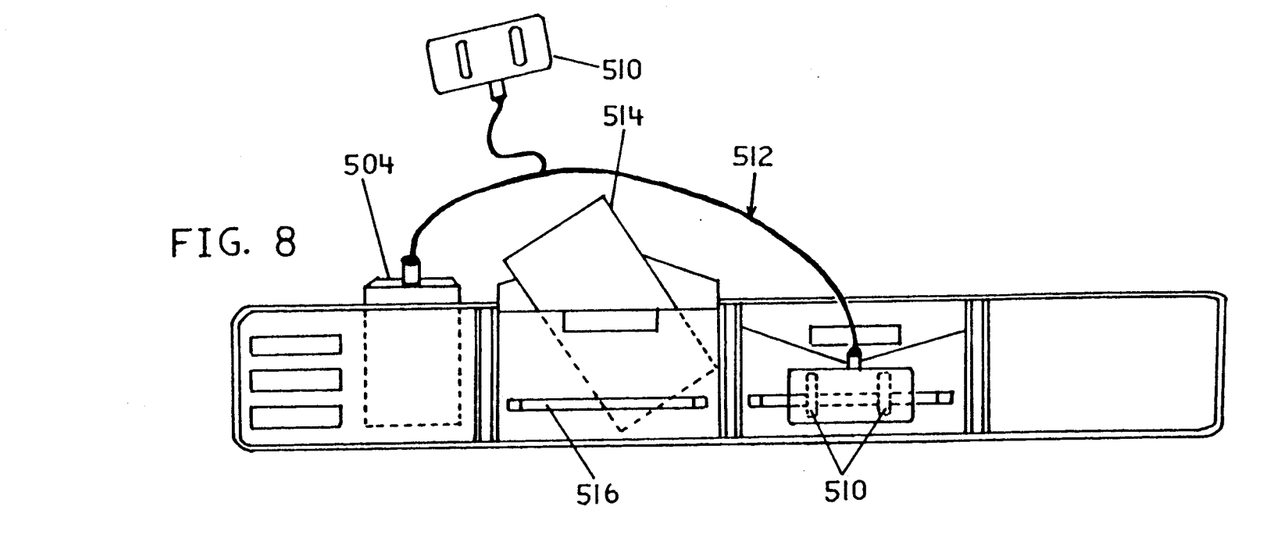
Figure 9:
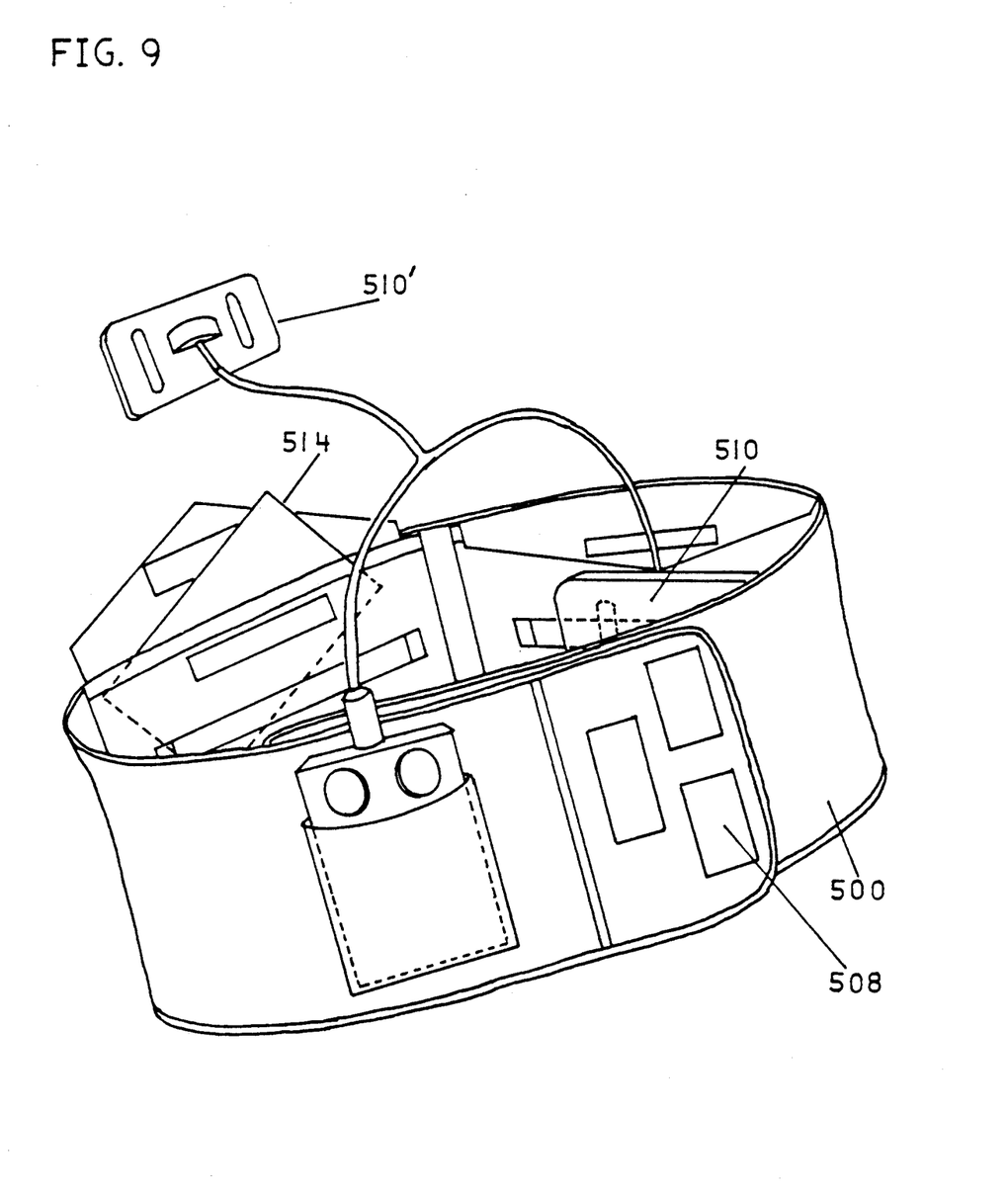
Figure 10:
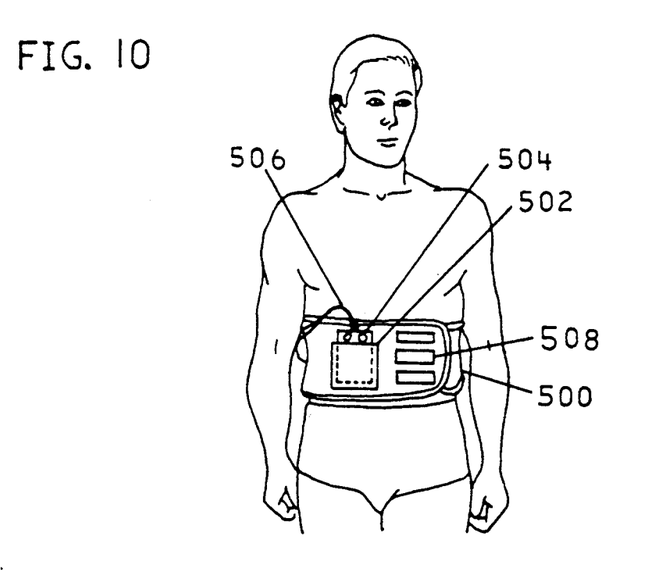

FIGS. 7-10 show a further embodiment of the present invention, wherein the electrical stimulator device and cold material are incorporated in a belt. FIGS. 7 and 8 respectively show opposite sides of the belt (the outside and inside of the belt, with respect to the belt in a closed position); FIG. 9 shows the belt in a closed position; and FIG. 10 shows the belt as worn by a person.

FIG. 7 shows belt 500 having, on the outside surface, a retention means 502 (for example, a pocket) for holding pulse generator 504. This FIG. 7 shows Velcro fastening means 508, for closing the belt in combination with a further fastening means on the opposite end of the belt. In FIG. 8 is shown the opposed side of the belt (which would be the inside when the belt is closed), having electrodes 510 which are connected to the pulse generator 504 by wire means 512. Also shown in FIG. 8 is an additional electrode means 510', which is not attached to the belt in FIG. 8; such electrode means 510' can be retained as desired on the retention means 516. Of course, such electrode means 510' can be positioned as desired on the skin surface of the body. Further shown in FIG. 8 is cold material (or hot material) 514, similar to the packet as described in connection with the second embodiment (that is, cold material 435 in FIG. 4). The cold material 514 can be replaceably held on the belt by retention means 516.

FIG. 9 shows the belt in a closed condition, showing the pulse generator 504 on the outside, with the cold material 514 and electrodes 510 on the inside. The belt positioned on a person is shown in FIG. 10. Similarly as with the other embodiments, it is highly desirable to have a tight fit of the belt against the person's body, so as to tightly hold the electrodes against the body. Accordingly, it is desired that the belt be made of elastic material, and that a fastening system be utilized which can achieve a tight fit against the body.

While the foregoing embodiments have been described in connection with use of electrical stimulation for increasing blood flow to surface regions of the body, with specific embodiments shown in connection therewith, the invention is not limited thereto. For example, and as indicated previously, packets of material having a relatively low pH (e.g., packets of material saturated with a liquid having a relatively low pH) can be held against portions of the body, so as to provide a material of relatively low pH at the skin surface and thereby increase flow of blood toward surface regions of the body. Illustratively, a non-irritating material (such as vinegar or lemon juice), having a pH in the range of 1.5-6.9, and a more preferred range of 2.0-5.8, can be applied to the skin surface for purposes of increasing blood flow to the surface regions of the body. Looking to the specific embodiments shown in FIGS. 7-10, the material for maintaining a relatively low pH adjacent the surface of the body can be held in the retention means 516 shown in FIG. 8. Alternatively, a further technique for increasing blood flow toward the skin surface includes application of a skin irritating means (a counter-irritant as known in the art) such as, for example, "Ben-Gay", which can be held against the body in the same manner as the material for maintaining a relatively high or relatively low pH.

Again, it is emphasized that the present invention is not limited to any specific techniques for increasing flow of blood toward the surface of the body, and generally contemplates the increase in flow of blood to a surface region of the body, in combination with application of heat or cold to the body, to improve heat transfer to the body, or from the body into the environment, particularly for specified purposes such as to increase burning of calories for purposes of increasing fat loss and resulting loss of weight.

As described previously, different techniques for increasing blood flow to surface regions of the body can be used simultaneously. Thus, a pad soaked with a relatively low pH, conducting liquid can be used both as an electrode for the electrical stimulation and for application of a relatively low pH material to the skin. Furthermore, such pad can be cooled (or heated) prior to application to the skin, so that the means for increasing flow of blood to surface regions of the body can also be used (e.g., simultaneously) for application of heat or cold to the body. Accordingly, a most simple and efficient heat transfer to or from the body can be achieved.

By the present invention, improved transfer of heat to or from a person's body can easily be achieved. More particularly, as a specific use of such technique, enhanced thermogenesis can be achieved due to the increased removal of heat from the body, whereby burning of calories in the body is further increased. Moreover, such increased burning of calories, by enhanced thermogenesis, can be utilized to increase loss of fat and increase weight loss. Thus, by the present invention, weight loss can be more easily and effectively caused, without intake of chemicals, such as drugs, and even independent of exercising. The present invention is essentially safe and can be used by most people to achieve fat, and weight, loss.

While I have shown and described several embodiments in accordance with the present invention, it is understood that the same is not limited thereto, but is susceptible of numerous changes and modifications as known to one having ordinary skill in the art, and I therefore do not wish to be limited to the details shown and described herein, but intend to cover all such modifications as are encompassed by the scope of the appended claims.

What is claimed is:

1. A method of increasing transfer of heat into or out of a body having blood circulating therethrough, comprising the steps of:
   (a) applying electrical stimulation to the body to increase amount of flow of the circulating blood to a surface region of the body; and
   (b) simultaneously with the application of electrical stimulation to increase amount of the flow of blood to the surface region, applying a heating medium or a cooling medium to said surface region of the body respectively to heat or cool the body, whereby, due to the increased amount of blood flow to the surface region caused by application of electrical stimulation, heat flow into or out of the body is increased, as compared to heat flow without application of electrical stimulation.

2. A method according to claim 1, wherein the body has muscles, and wherein the electrical stimulation applied to the body is an electrical stimulation of muscles in the body.

3. A method according to claim 1, wherein the electrical stimulation is electrical pulses, applied at a frequency of 1 pulse/ten minutes, to 100,000 Hz.

4. A method according to claim 3, wherein the electrical pulses have a pulse width of 0.01-60,000 microseconds, and an amplitude of 0.001-2,000 milliampere.

5. A method according to claim 3, wherein the electrical pulses are applied at a frequency of 1-10 Hz.

6. A method according to claim 1, wherein the body is a human, the heating medium or cooling medium is applied to the human by forcing air, of a temperature above or below human body temperature, respectively, to flow against the body.

7. A method according to claim 1, wherein the application of electrical stimulation to the body includes contacting electrodes to the body, the electrodes including a conducting liquid having a pH of 1.5-6.9, in contact with the body.

8. A method according to claim 1, wherein the heating medium or cooling medium is applied to said surface of the body by immersing the body in a fluid medium that is said heating medium or said cooling medium.

9. A method according to claim 8, wherein said fluid medium is water.

10. A method of burning calories in a body having blood circulating therethrough, comprising the steps of:
(a) applying electrical stimulation to the body to increase amount of the flow of blood to a surface region of the body; and
(b) simultaneously with applying electrical stimulation to the body to increase the amount of flow of blood to the surface region, applying a cooling medium to the surface region such that, due to the increased amount of blood flow to the surface region caused by the electrical stimulation, flow of heat from the body is increased, whereby an increased burning of calories is achieved, as compared to the burning of calories when applying the cooling medium without applying the electrical stimulation.

11. A method according to claim 10, wherein the body is a person who is exercising, and wherein the steps of increasing the flow of blood and applying a cooling medium are performed simultaneously while the person is exercising.

12. A method according to claim 10, wherein the body is a human, and wherein the cooling medium is applied by forcing cool air, at a temperature less than human body temperature, to flow against the body.

13. A method according to claim 10, wherein the application of electrical stimulation to the body includes contacting electrodes to the body, the electrodes including a conducting liquid having a pH of 1.5-6.9, in contact with the body.

14. A method according to claim 10, wherein the cooling medium is applied to the surface region by immersing the body in a fluid medium that is said cooling medium.

15. A method according to claim 14, wherein said fluid medium is water.

16. Apparatus for transfer of heat into or out of a body having blood circulating therethrough, comprising:
(a) means for applying electrical stimulation to a surface region of the body to increase amount of flow of blood to the surface region of the body, said means for applying electrical stimulation being a means for applying a pulsed electrical current to the body;
(b) a substrate, for holding said means for applying electrical stimulation against the body; and
(c) means for applying a heating or cooling medium to said surface region of the body, such that, due to the increased amount of blood flow caused by the electrical stimulation means, transfer of heat into or out of the body, respectively, is increased, as compared to the transfer of heat without application of the electrical stimulation means.

17. Apparatus according to claim 16, wherein said means for applying a heating or cooling medium to the body is a fan means for forcing circulation of the heating or cooling medium against the body.

18. Apparatus according to claim 16, wherein said substrate is a body suit.

19. Apparatus according to claim 18, wherein said body suit is a mesh body suit, made of an elastic material so as to hold said means against the body.

20. Apparatus according to claim 16, wherein said substrate is a vest.

21. Apparatus according to claim 16, wherein said substrate is a belt.

22. Apparatus according to claim 16, wherein said substrate also includes means for holding the means for applying a heating or cooling medium, so as to heat or cool the body.

23. Apparatus according to claim 22, wherein the means for holding the means for applying a heating or cooling medium is a means for replaceably holding said heating or cooling medium.

24. Apparatus according to claim 16, wherein said body includes skin as a surface thereof, and wherein said electrical stimulation means includes an electric pulse generator means, at least one pair of electrode means on said substrate and caused to be in contact with the skin of the body by said substrate, and wiring means for transmitting pulsed electrical current from the generator means to the at least one pair of electrode means, whereby pulsed electrical current is caused to flow through the body.

25. Apparatus according to claim 24, wherein a plurality of said pair of electrode means are provided on said substrate and are electrically connected by said wiring means to said electric pulse generator means.

26. Apparatus according to claim 24, wherein the pulsed generator is enclosed in a waterproof case, whereby the apparatus can be used underwater.

27. Apparatus according to claim 16, wherein said electrical stimulation means includes at least one pair of electrode means in contact with the body, said at least one pair of electrode means including a conducting liquid having a pH of 1.5-6.9 in contact with the body, whereby the conducting liquid can be used both as electrode means for the electrical stimulation and for application of a relatively low pH material to the body.

28. A method of increasing transfer of heat into or out of a body having blood circulating through the body, comprising the steps of:
(a) locally contacting a material having a pH of 1.5-6.9 to the body to increase amount of flow of the circulating blood to a surface region of the body; and
(b) simultaneously with the local contact to increase the amount of the flow of blood to the surface region, applying a heating medium or a cooling medium to said surface region of the body respectively to heat or cool the body, whereby, due to the increased amount of blood flow to the surface region caused by the local contact, heat flow into or out of the body is increased, as compared to heat flow without the local contact.

29. A method according to claim 28, wherein the heating medium or cooling medium is locally applied to a same portion of the body locally contacted with said material of pH of 1.5-6.9.

30. A method according to claim 28 wherein said material is a liquid having a pH of 1.5-6.9.

31. A method according to claim 28, wherein said material has a pH of 2.0–5.8.

32. Apparatus for transfer of heat into or out of a body having blood circulating therethrough, comprising:
  (a) means for locally applying a material of pH ob 1.5–6.9 to the body to increase amount of flow of blood to a surface region of the body;
  (b) a substrate, for holding said means for locally applying a material of pH of 1.5–6.9 against the body; and
  (c) means for applying a heating or cooling medium to said surface region of the body, such that, due to the increased amount of blood flow caused by the local application, transfer of heat into or out of the body, respectively, is increased, as compared to the transfer of heat without the local application.

33. A method of increasing transfer of heat into or out of a body having blood circulating therethrough, the body having skin as a surface thereof, comprising the steps of:
  (a) locally applying a counter-irritant to the body to increase flow of the circulating blood to a surface region of the body; and
  (b) simultaneously with the local application of a counter-irritant to increase the flow of blood to the surface region, applying a heating medium or a cooling medium to said surface region of the body respectively to heat or cool the body, whereby, due to the increased amount of flow of blood to the surface region caused by local application of the counter-irritant, heat flow into or out of the body is increased, as compared to heat flow without local application of the counter-irritant.

34. Apparatus for transfer of heat into or out of a body having blood circulating therethrough, the body having skin as a surface thereof, comprising:
  (a) means for locally applying a counter-irritant to the body to increase amount of flow of blood to a surface region of the body;
  (b) a substrate, for holding said means for locally applying a counter-irritant against the body; and
  (c) means for applying a heating or cooling medium to said surface region of the body, such that, due to the increased amount of blood flow caused by the local application of a counter-irritant, transfer of heat into or out of the body, respectively, is increased, as compared to transfer of heat without local application of the counter-irritant.

* * * * *